US008852551B2

(12) United States Patent
Jordan

(10) Patent No.: US 8,852,551 B2
(45) Date of Patent: *Oct. 7, 2014

(54) METHODS TO IMPAIR HEMATOLOGIC CANCER PROGENITOR CELLS AND COMPOUNDS RELATED THERETO

(75) Inventor: Craig Jordan, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/636,263

(22) Filed: Dec. 11, 2009

(65) Prior Publication Data

US 2010/0093003 A1  Apr. 15, 2010

Related U.S. Application Data

(63) Continuation of application No. 10/830,089, filed on Apr. 23, 2004, now Pat. No. 7,651,678, which is a continuation of application No. 09/799,100, filed on Mar. 6, 2001, now Pat. No. 6,733,743.

(60) Provisional application No. 60/187,123, filed on Mar. 6, 2000, provisional application No. 60/227,295, filed on Aug. 24, 2000.

(51) Int. Cl.
| A61K 51/00 | (2006.01) |
| A61K 39/395 | (2006.01) |
| C07K 16/28 | (2006.01) |
| A61K 51/10 | (2006.01) |
| A61K 39/00 | (2006.01) |

(52) U.S. Cl.
CPC ....... *C07K 16/2866* (2013.01); *A61K 39/39558* (2013.01); *A61K 51/1033* (2013.01); *A61K 51/1096* (2013.01); *A61K 2039/505* (2013.01)
USPC ............ 424/1.49; 424/143.1; 424/153.1; 424/155.1; 424/173.1; 424/183.1

(58) Field of Classification Search
None
See application file for complete search history.

(56) References Cited

U.S. PATENT DOCUMENTS

| 4,340,535 A | 7/1982 | Voisin et al. |
| 5,489,516 A | 2/1996 | Broudy et al. |
| 6,733,743 B2 | 5/2004 | Jordan |
| 7,651,678 B2 * | 1/2010 | Jordan .................. 424/1.49 |

FOREIGN PATENT DOCUMENTS

WO  WO97/24373  7/1997

OTHER PUBLICATIONS

Feldman et al Transplant. Proc. 1998, 30, 4126-4127.*
Cochlovius et al ., Modern Drug Discovery, 2003, pp. 33-38.*
Sun et al., "Monoclonal antibody 7G3 recognizes the N-terminal domain of the human interleukin-3 (IL-3) receptor alpha-chain and functions as a specific IL-3 receptor antagonist," 1996, Blood, 87:83-92.
Jordan et al., "The interleukin-3 receptor alpha chain is highly expressed on primitive acute myelogenous leukemia," 1999, Blood, 94:67A.
Chan et al., "Reactivity of murine cytokine fusion toxin, diphtheria toxin390-murine interleukin-3 (DT390-mIL-3), with bone marrow progenitor cells," 1996, Blood, 88:1445-1456.
Koubek et al., "Occurrence of cytokine receptors on different lymphoid leukaemic cells," 1999, Eur. J. Hematol., 63:1-10.
Tweardy et al., "Modulation of myeloid proliferation and differentiation by monoclonal antibodies directed against a protein that interacts with the interleukin-3 receptor," 1992, Blood, 80:359-366.
Rosenblum et al., "Recombinant immunotoxins directed against the c-erb-2/HER2/neu oncogene product: in vitro cytotoxicity, pharmacokinetics, and in vivo efficacy studies in xenograft models," 1999, Cin. Cancer Res., 5:865-874.
European Search Report issued in European Patent Application No. 01923325.3-1222 dated Sep. 26, 2008.

* cited by examiner

*Primary Examiner* — Michail Belyavskyi
(74) *Attorney, Agent, or Firm* — Jones Day

(57) ABSTRACT

Primitive or progenitor hematologic cancer cells have been implicated in the early stages and development of leukemia and malignant lymphoproliferative disorders, including acute myelogenous leukemia (AML), chronic myelogenous leukemia (CML) and chronic lymphoid leukemia (CLL). Interleukin-3 receptor alpha chain (IL-3Rα or CD123) is strongly expressed on progenitor hematologic cancer cells, but is virtually undetectable on normal bone marrow cells. The present invention provides methods of impairing progenitor hematologic cancer (e.g., leukemia and lymphomic) cells by selectively targeting cells expressing CD123. These methods are useful in the detection and treatment of leukemias and malignant lymphoproliferative disorders. Also provided are compounds useful for selectively binding to CD123 and impairing progenitor hematologic cancer cells. These compounds may include cytotoxic moieties such as, for example, radioisotopes or chemotherapeutics.

10 Claims, 8 Drawing Sheets

METHODS TO IMPAIR HEMATOLOGIC CANCER PROGENITOR CELLS AND COMPOUNDS RELATED THERETO

CONTINUING DATA

The present application is a continuation of U.S. application Ser. No. 10/830,089, filed Apr. 23, 2004, now U.S. Pat. No. 7,651,678, which is a continuation of U.S. application Ser. No. 09/799,100, filed Mar. 6, 2001, now U.S. Pat. No. 6,733,743, which claims the benefit of priority to U.S. Provisional Patent Application Nos. 60/187,123, filed Mar. 6, 2000, and 60/227,295, filed Aug. 24, 2000, the disclosures of each of which are incorporated by reference herein in their entirety.

BACKGROUND OF THE INVENTION

1. Field of the Invention

The present invention is related to methods of impairing progenitor hematologic cancer cells or treating hematologic cancer by targeting a cell surface marker specific for progenitor hematologic cancer cells. The present invention is also related to a method for diagnosing hematologic cancer.

2. Background of the Invention

Stem cells are commonly found in a variety of mammalian tissue systems. While the criteria by which such cells are defined vary depending upon the specific context, two properties are generally regarded as central features of stem cell populations: (1) stem cells must exhibit some capacity for self-replication or self-renewal, and (2) stem cells must be capable of differentiating into appropriate lineages (Potten C S: Stem Cells. London, Academic Press, 1997). Cells of this nature have been described for a number of tissues including hematopoietic, embryonic, neural, muscle and hepatic systems (Lemischka I R. Clonal, in vivo behavior of the totipotent hematopoietic stem cell. Semin Immunol 1991, 3: 349-55; Morrison S J, et al., The biology of hematopoietic stem cells. Annu. Rev. Cell Dev. Biol. 1995, 11: 35-71; Robertson E J., Using embryonic stem cells to introduce mutations into the mouse germ line. Biol Reprod 1991, 44: 238-45; Gage F H., Mammalian neural stem cells. Science 2000, 287: 1433-8; and, Alison M, et al., Hepatic stem cells. J Hepatal 1998, 29: 676-82). Thus, it is perhaps not surprising that similar cells have recently been documented in the context of malignant populations (Bonnet D, et al., Human acute myeloid leukemia is organized as a hierarchy that originates from a primitive hematopoietic cell. Nat. Med. 1997, 3: 730-737; Blair A, et al., Most acute myeloid leukemia progenitor cells with long-term proliferative ability in vitro and in vivo have the phenotype CD34(+)/CD71(−)/HLA-DR−. Blood 1998, 92: 4325-35; Cobaleda C, et al., A primitive hematopoietic cell is the target for the leukemic transformation in human Philadelphia-positive acute lymphoblastic leukemia. Blood 2000, 95: 1007-13). Indeed, a stem cell is in some respects the ideal target for malignant transformation in that relatively little biological change is required. Since stem cells already possess the genetic programming necessary to be highly proliferative and developmentally plastic, one can imagine that relatively subtle perturbations might be sufficient to induce disease.

One example of neoplasia arising from malignant stem cells has recently been documented in the hematopoietic system in the case of acute myelogenous leukemia (AML). This disease is characterized by premature arrest of myeloid development and the subsequent accumulation of large numbers of non-functional leukemic blasts. While leukemic blast cells are often of clonal origin and display relatively homogeneous features, it has been demonstrated that such populations are organized in a hierarchical fashion, analogous to normal hematopoietic progenitors. Thus, there is a phenotypically defined leukemic stem cell population that is sufficient to propagate leukemic blasts both in vitro and in vivo in xenogeneic mouse models of human AML (Bonnet D, et al., Human acute myeloid leukemia is organized as a hierarchy that originates from a primitive hematopoietic cell. Nat. Med. 1997, 3: 730-737; Blair A, et al., Most acute myeloid leukemia progenitor cells with long-term proliferative ability in vitro and in vivo have the phenotype CD34(+)/CD71(−)/HLA-DR−. Blood 1998, 92: 4325-35, Cobaleda C, et al., A primitive hematopoietic cell is the target for the leukemic transformation in human Philadelphia-positive acute lymphoblastic leukemia. Blood 2000, 95: 1007-13; Blair A, et al. Lack of expression of Thy-1 (CD90) on acute myeloid leukemia cells with long-term proliferative ability in vitro and in vivo. Blood 1997, 89: 3104-12). The concept of a leukemic stem cell (LSC) becomes critically important in considering the etiology of human disease. Clearly, in order to achieve durable remission, it will be necessary to specifically ablate the primitive or progenitor LSC population. However, previous studies (Terpstra W, et al., Fluorouracil selectively spares acute myeloid leukemia cells with long-term growth abilities in immunodeficient mice and in culture. Blood 1996, 88: 1944-50), as well as data from our group, suggest that LSC's are biologically distinct from more mature leukemic blasts and may not be responsive to conventional chemotherapeutic regimens. This observation is consistent with the clinical profile frequently seen for AML, wherein a majority of patients can achieve apparent complete remission, but in most cases will relapse (Schiller G J., Treatment of resistant disease. Leukemia 1998, 12 Suppl 1: S20-4; Paietta E., Classical multidrug resistance in acute myeloid leukemia. Med Oncol 1997, 14: 53-60). If LSC's are more refractile to chemotherapy than blasts, it is attractive to propose that surviving stem cells are a major contributing factor to leukemic relapse. Thus, strategies that specifically target progenitor leukemia cells may provide more effective treatment for leukemia patients. In 1997, Bonnet and Dick described the phenotype for LSC's as CD34+/CD38− (Bonnet D, et al., Human acute myeloid leukemia is organized as a hierarchy that originates from a primitive hematopoietic cell. Nat. Med. 1997, 3: 730-737). We report that the IL-3 receptor alpha chain (CD123) is highly expressed on leukemic but not normal CD34+/CD38− hematopoietic cells. In view of this state of the art, there is a need in the art to provide a diagnostic method for detecting leukemia at an early stage, as well as more effective methods of treating this disease.

SUMMARY OF THE INVENTION

The present invention relates to a method of using compounds that bind to the human CD123 molecule (CD123 ectopeptide), in the diagnosis and treatment of hematologic cancers (e.g., leukemias and malignant lymphoproliferative disorders). The CD123 specific compounds and mimetics have particular utility as pharmaceuticals and reagents for the therapy of hematologic cancer or malignant disease states and for the diagnosis of hematologic cancer disease states. In one embodiment, the present invention provides a method of impairing a hematologic cancer progenitor cell comprising contacting the cell with a compound that selectively binds to CD123 in an amount effective to impair the progenitor hematologic cancer cell. This contacting step may occur in various environments, including in vitro and in vivo in the body of an animal, including a human.

Throughout this application, reference will be made specifically to leukemia in describing certain embodiments of the present invention. However, it is understood that the present invention is not limited to diagnosis and treatment of leukemia or malignant lymphoproliferative disorders alone, but to any disease in which the cancerous cells selectively express CD123, which includes the genus of hematologic cancer.

In one embodiment, the present invention is directed to a method of detecting the presence of CD123 on, for example, a leukemia progenitor cell. Thus, the invention is also directed to a method of diagnosing leukemia. It is understood that by using a labeled ligand to bind to CD123, it is possible to detect the presence of leukemia progenitor cells. Thus, it is also possible to diagnose the likelihood of the onset of leukemia in patients possessing such leukemic progenitor cells expressing CD123. The CD123 binding ligand may be an antibody to CD123, or it may be any of a variety of molecules that specifically bind to CD123. Furthermore, the label can be chosen from any of a variety of molecules, including, but not limited to, enzymatic compounds, or non-enzymatic compounds that serve as a reporter of the presence of the ligand which has bound to the CD123 molecule. Examples of such labels include those that are, for example, radioactive, fluorescent, chemiluminescent or absorbant-based, or a combination of the foregoing. In one embodiment, an assay is provided for detecting the presence of progenitor leukemia cells in a sample by detecting the presence of CD123 in the sample, which may be accomplished by introducing a compound that selectively binds to CD123 and determining whether the compound binds to a component of the sample.

In another series of embodiments, the present invention also provides compounds or molecules which mimic (mimetics) the three-dimensional structure of part or all of the compounds such as peptides, antibodies, carbohydrates, lipids or nucleic acids that bind to CD123, and in the case of antibodies, of the binding pockets of the antibodies, or of the complementarity determining regions (CDR's).

The present invention also provides pharmaceutical preparations comprising a pharmaceutically acceptable carrier; and any one or more of the CD123 specific compounds and mimetics described above.

In another set of embodiments, the present invention provides a method for the treatment of leukemia, comprising administering to a human subject or other animal in need of such treatment a therapeutically effective amount of the compounds or their mimetic pharmaceutical compositions described above.

In still another set of embodiments, the present invention provides a method of selectively purging leukemic stem cells from bone marrow. These stems cells may give rise to leukemia progenitor cells, or they may be the progenitor cells, which may be impaired by the method of the invention using various compounds or their mimetics and cytotoxic agents that may be contacted to either a bone marrow sample or injected into a bone marrow of an individual, thereby destroying at least some of the leukemic stem cells in the bone marrow.

BRIEF DESCRIPTION OF THE DRAWINGS

The present invention will become more fully understood from the detailed description given herein below, and the accompanying drawings which are given by way of illustration only, and thus are not limiting of the present invention, and wherein.

DETAILED DESCRIPTION OF THE INVENTION

Definitions

Figure 1A:
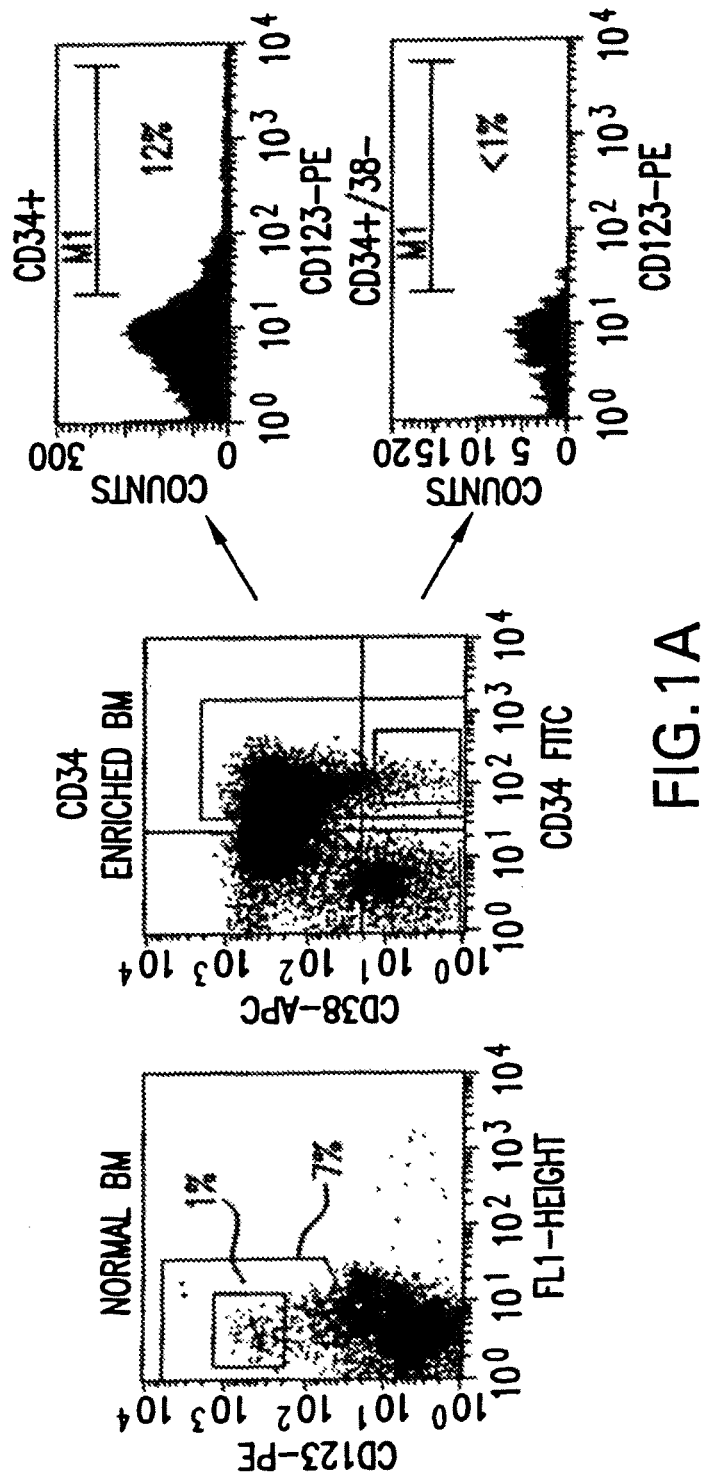
FIGS. 1A and 1B show CD123 expression on normal and leukemic hematopoietic cells. Representative examples of CD123 labeling in cells derived from normal bone marrow (panel A) or primary AML peripheral blood (panel B) are provided. The inset polygon in panel A (left dot plot) indicates the percentage of total bone marrow that is positive for CD123 expression (7%). The smaller rectangular gate indicates the proportion of total marrow strongly positive for CD123 (1%). The center dot plot in panel A shows bone marrow that was enriched for CD34+ cells by selection on an immunoaffinity column (see methods). The gates indicate the total CD34+ population and the CD34+/CD38− population. The histograms indicate the CD123 labeling for the two gated populations. Panel B shows the same analysis for the primary AML specimen. M1 markers in the histograms indicate expression levels that are higher than 99% of isotype control samples. For each specimen, 50,000-100,000 events were analyzed.

As used herein, the term "antibody" means an immunoglobulin molecule, or a fragment of an immunoglobulin molecule, having the ability to specifically bind to a particular antigen. Antibodies are well known to those of ordinary skill in the science of immunology. As used herein, the term "antibody" means not only intact antibody molecules but also fragments of antibody molecules retaining antigen-binding ability. Such fragments are also well known in the art and are regularly employed both in vitro and in vivo. In particular, as used herein, the term "antibody" means not only intact immunoglobulin molecules but also the well-known active fragments $F(ab')_2$, Fab, Fv, Fd, $V_H$ and $V_L$.

As used herein, the terms "bind" or "bind(s)" shall mean any interaction, whether via direct or indirect means, which affects the specified receptor or receptor subunit.

As used herein, the terms "binds selectively to" shall mean that the compound, composition, formulation, etc. does not significantly bind IL3R beta chain, but does bind IL3R alpha chain.

As used herein, the terms "CD123", "IL3R subunit alpha" and "IL3Rα" shall be used interchangeably to mean an antigenic determinant that is detectable in leukemia precursor cells as described herein, but not detectable on normal cells as described herein.

As used herein, the term "compound" shall mean any purity of active ingredient, including formulations, compositions, naturally-occurring plants or animals, etc. The compound may include molecules that are naturally occurring, such as proteins, nucleic acids, single stranded nucleic acids, lipids, carbohydrates, and antibodies. However, synthetic versions of these naturally occurring molecules may be made, so long as they bind CD123. The compounds may comprise more than one component. For example, a compound may be a monoclonal antibody attached to a toxin. Or, it may be a lipid attached to a label. The compounds may further comprise mimetics, and aptamers, but which all retain their specificity to CD123.

As used herein, the term "impair" shall mean any decrease in functionality or activity (including growth or proliferative activity).

As used herein, the term "hematologic cancer" refers to a cancer of the blood, and includes leukemia and malignant lymphoproliferative disorders, among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Cancer cells in acute leukemias are blocked at an immature stage. However, they continue to multiply. Consequently, there is a large accumulation of non-functional immature cells and the concomitant loss of functional cells. Chronic leukemias progress more slowly, with cancer cells developing to full maturity. Furthermore, the white blood cells may be myelogenous or lymphoid. Thus, certain forms of leukemia may be, by way of example, acute lymphatic (or lymphoblastic) leukemia (ALL); acute myelogenic leukemia (AML); chronic lymphocytic leukemia (CLL); or chronic myelogenic leukemia (CML); and myelodysplastic syndrome. "Malignant lymphoproliferative disorders" may refer to a lymphoma, such as multiple myeloma, non-Hodgkin's lymphoma, Burkitt's lymphoma, and follicular lymphoma (small cell and large cell), among others. For purposes of this invention, at least some of the hematologic cancer cells are characterized by cells that express CD123. Also, for the purposes of this application, whenever leukemia or malignant lymphoproliferative disorders are mentioned, the diagnostic and treatment method of the invention applies generally to hematologic cancer.

As used herein, the term "introducing" shall mean any means of delivery, whether in vivo or in vitro, including simple contact.

As used herein, the term "mimetic" means a compound or molecule which mimics the three-dimensional structures of a site on CD123 to which a compound may bind, or the compound may be a molecule that mimics a molecule that binds to CD123. In the case of an anti-CD123 antibody binding site, or paratope, or active site, "mimetic" means a compound that mimics the three-dimensional structure of any combination of the antibody hypervariable loops or complementarity determining regions (CDR's).

As used herein, the term "mimic" means the three-dimensional placement of atoms of the mimetic such that similar ionic forces, covalent forces, van der Waal's or other forces, and similar charge complementarity, or electrostatic complementarity, exist between the atoms of the mimetic and the atoms of the binding site of the compound such as a peptide or an antibody such that the mimetic has a similar binding affinity for CD123 as the parent compound and/or such that the mimetic has a similar effect on the function of CD123 in vitro or in vivo.

In the case of anti-CD123 antibodies, within the antigen-binding portion of an antibody, as is well-known in the art, there are complementarity determining regions (CDRs), which directly interact with the epitope of the antigen, and framework regions (FRs), which maintain the tertiary structure of the paratope. In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

As used herein, the term "normal" means any non-pathogenic or non-pathology-related cells or conditions.

As used herein, the terms "primitive" and "progenitor" shall be interchangeable. As used herein, with respect to polypeptides and antibodies, the term "substantially pure" means that the polypeptides are substantially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a small percentage by weight of the preparation.

The polypeptide is nonetheless substantially pure in that it has been substantially separated from the substances with which it may be associated in living systems.

As used herein with respect to compounds or mimetics, the term "substantially pure" means that the compounds are substantially free of other substances with which they may be found, in nature, in in vivo systems; or as a result of chemical or other synthesis, to an extent practical and appropriate for their intended use. In particular, the compounds are sufficiently pure and are sufficiently free from other biological constituents of their hosts cells, or chemical or physical constituents of their synthesis so as to be useful in, producing pharmaceutical preparations. By techniques well known in the art (U.S. Pat. No. 5,648,379; Colman, P. G. *Protein Science* 3: 1687-1696, 1994; Malby, et al., *Structure* 2: 733-746, 1994; McCoy et al., *J. Molecular Biol.* 268: 570-584, 1997), substantially pure compounds or mimetics, may be designed. Because a substantially purified compound of the invention may be admixed with a pharmaceutically acceptable carrier in a pharmaceutical preparation, the compound may comprise only a small percentage by weight of the preparation. The compound is nonetheless substantially pure in that it has been substantially separated from the substances with which it may be associated in living, chemical or other systems.

Mimetics That Bind to CD123

Compounds that target CD123 can be found. Phage display libraries can be used to determine the DNA encoding the polypeptide that binds to CD123. The principles of this approach are disclosed in U.S. Pat. No. 5,837,500, which is incorporated by reference herein in its entirety. Other non-peptide molecules that may bind to CD123 include nucleic acids, and liposomes. Carbohydrates may also be used to target CD123. It is possible that the compound may not be a naturally occurring biological molecule. Such chemicals may be made by combinatorial libraries which are well known in the art, with the assay goal being the binding of the chemical compound to CD123. Liposomes may ensconce certain toxins or other cell-impairing substances or cell-imaging compounds may be used to target CD123. Numerous variations and combinations of compounds as targeting agents are contemplated by the method of the invention, so long as CD123 is targeted, with the knowledge that leukemia detection and leukemia treatment is kept in mind.

Mimetics of Anti-CD123 Antibodies

It is also possible to use the anti-idiotype technology to isolate or screen for compounds or mimetics which mimic an epitope. Thus, an anti-idiotypic monoclonal antibody which is the image of the epitope bound by the first monoclonal antibody, since it effectively acts as an antigen, may be used to isolate mimetics from a combinatorial chemical, or other libraries, of chemical or other compounds, such as peptide phage display libraries (Scott and Smith, *Science* 249: 386-390, 1990; Scott and Craig, *Curr. Opin. Biotechnol.* 5: 40-48, 1992; Bonnycastle et al., *J. Mol. Biol.* 258: 747-762, 1996). Hence, peptides or constrained peptides mimicking proteins or other compounds, including those with nucleic acid, lipid, carbohydrate or other moieties, may be cloned (Harris et al., *Proc. Natl. Acad. Sci.* (*USA*) 94: 2454-2459, 1997).

Purely synthetic molecules, which may not occur in nature and are therefore more resistant to catabolism, excretion or degradation, may be designed by the three-dimensional placement of atoms, such that similar ionic forces, covalent forces, van der Waal's or other forces, and similar charge complementarity, or electrostatic complementarity, exist between the atoms of the mimetic and the atoms of the antigenic binding site or epitope. These mimetics may then be screened for high affinity binding to CD123 and detect and/or impair the CD123 bearing cell in vitro or in vivo, as described in more detail below.

Diagnostic and Pharmaceutical Preparations

The invention also relates to a method for preparing diagnostic or pharmaceutical compositions comprising the CD123 binding compound and its mimetics. The pharmaceutical preparation includes a pharmaceutically acceptable carrier. Such carriers, as used herein, mean non-toxic materials that do not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials that are well known in the art.

The anti-CD123 antibodies and mimetics may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the CD123 binding compound, such as monoclonal antibodies, or mimetics thereof, or will be able to ascertain such, using routine experimentation. Furthermore, the binding of these labels to the CD123 specific compounds or their mimetics can be done using standard techniques common to those of ordinary skill in the art.

In the case of antibodies, another labeling technique which may result in greater sensitivity consists of coupling the antibodies or mimetics to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Diagnostic and Treatment Kits

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a compound that binds to CD123, such as a monoclonal antibody, or a mimetic thereof, which is, or can be, detectably labeled with a label that is suitable for diagnostic purposes or if treatment is desired, a cytotoxic or impairing agent. In the case of a diagnostic kit, the kit may also have containers containing buffer(s) and/or a container comprising a reporter-means, such as a biotin-binding protein, such as avidin or streptavidin, bound to a reporter molecule, such as an enzymatic or fluorescent label. In addition to the chemical material, of course a means of instructions for using the kit is included, preferably for either diagnosing leukemia, or treating leukemia. The instruction means may be written on the vial, tube and the like, or written on a separate paper, or on the outside or inside of the container. The instructions may also be in the form of a multi-media format, such as CD, computer disk, video and so on.

Preparation of Immunotoxins

While the preparation of immunotoxins is, in general, well known in the art (see, e.g., U.S. Pat. No. 4,340,535, and EP 44167, both incorporated herein by reference), the inventors are aware that certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known which can successfully be employed to conjugate the toxin moiety with the binding agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

Cross-linking reagents are used to form molecular bridges that tie together functional groups of two different proteins (e.g., a toxin and a binding agent). To link two different proteins in a step-wise manner, hetero bifunctional cross-linkers can be used which eliminate the unwanted homopolymer formation. An exemplary hetero bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., dgA).

The spacer arm between these two reactive, groups of any cross-linkers may have various lengths and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

The most preferred cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido)ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane. The use of such cross-linkers is well understood in the art.

Once conjugated, it will be important to purify the conjugate so as to remove contaminants such as unconjugated A chain or binding agent. It is important to remove unconjugated A chain because of the possibility of increased toxicity. Moreover, it is important to remove unconjugated binding agent to avoid the possibility of competition for the antigen between conjugated and unconjugated species. In any event, a number of purification techniques are disclosed in the Examples below which have been found to provide conjugates to a sufficient degree of purity to render them clinically useful. In general, the most preferred technique will incorporate the use of Blue-Sepharose with a gel filtration or gel permeation step. Blue-Sepharose is a column matrix composed of Cibacron Blue. 3GA and agarose, which has been found to be useful in the purification of immunoconjugates. The use of Blue-Sepharose combines the properties of ion exchange with A chain binding to provide good separation of conjugated from unconjugated binding.

The Blue-Sepharose allows the elimination of the free (non conjugated) binding agent (e.g., the antibody or fragment) from the conjugate preparation. To eliminate the free (unconjugated) toxin (e.g., dgA) a molecular exclusion chromatography step is preferred using either conventional gel filtration procedure or high performance liquid chromatography.

After a sufficiently purified conjugate has been prepared, one will desire to prepare it into a pharmaceutical composition that may be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less than 0.5 ng/mg protein. Moreover, for human administration, preparations should meet sterility, pyrogenicity, general safety and purity standards as required by FDA Office of Biological Standards.

A preferred parenteral formulation of the immunotoxins in accordance with the present invention is 0.25 to 2.5 mg conjugate/ml in 0.15M NaCl aqueous solution at pH 7.5 to 9.0. The preparations may be stored frozen at −10° C. to −70° C. for at least 1 year.

It is contemplated that most therapeutic applications of the present invention will involve the targeting of a toxin moiety (cytotoxic agent) to the CD123 leukemia marker. This is due to the much greater ability of most toxins to deliver a cell killing effect as compared to other potential agents.

However, there may be circumstances such as when the target antigen does not internalize by a route consistent with efficient intoxication by immunotoxins, where one will desire to target chemotherapeutic agents such as cytokines, antimetabolites, alkylating agents, hormones, and the like. The advantages of these agents over their non-antibody conjugated counterparts is the added selectivity afforded by the antibody. One might mention by way of example agents such as steroids, cytosine arabinoside, methotrexate, aminopterin, anthracyclines, mitomycin C, vinca alkaloids, demecolcine, etopside, mithramycin, and the like. This list is, of course, merely exemplary in that the technology for attaching pharmaceutical agents to antibodies for specific delivery to tissues is well established.

One preferred cytotoxic moiety for use in the present invention is a radioisotope, which can be coupled to or conjugated with, for example, an anti-CD123 antibody. Preferred radioisotopes include α-emitters such as, for example, $^{211}$Astatine, $^{212}$Bismuth and $^{213}$Bismuth, as well as β-emitters such as, for example, $^{131}$Iodine, $^{90}$Yttrium, $^{177}$Lutetium, $^{153}$Samarium and $^{109}$Palladium. Particularly preferred radioisotopes are $^{211}$Astatine and $^{131}$Iodine.

It is proposed that particular benefits may also be achieved through the application of the invention to cell imaging. Imaging of leukemia cells is believed to provide a major advantage when compared to available imaging techniques, in that the cells are readily accessible.

Moreover, the technology for attaching paramagnetic, radioactive and even fluorogenic ions to antibodies is well established. Many of these methods involve the use of a metal chelate complex employing, for example, an organic chelating agent such a DTPA attached to the antibody (see, e.g., U.S. Pat. No. 4,472,509). In the context of the present invention the selected ion is thus targeted to the cancerous area by the antibody, allowing imaging to proceed by means of the attached ion.

In a preferred embodiment, in the method of the invention, the antibodies may also be fused to a protein effector molecule by recombinant means such as through the use of recombinant DNA techniques to produce a nucleic acid which encodes both the antibody and the effector molecule and expressing the DNA sequence in a host cell such as *E. coli*. The DNA encoding the chimeric protein may be cloned in cDNA or in genomic form by any cloning procedure known to those skilled in the art. See for example Sambrook et al., Molecular Cloning: A Laboratory Manual, Cold Spring Harbor Laboratory, (1989), which is herein incorporated by reference.

Fusion or conjugation of antibodies to various labels produces a highly specific detectable marker that may be used to detect the presence or absence of cells or tissues bearing the particular molecule to which the antibody is detected. Alternatively, the antibodies may be chemically conjugated or fused to an effector molecule that is another specific binding moiety, e.g. a ligand such as those described above. In this form the composition will act as a highly specific bifunctional linker. This linker may act to bind and enhance the interaction between cells or cellular components to which the fusion protein binds. Thus, for example, where the fusion protein is a growth factor joined to an antibody or antibody fragment (e.g. an Fv fragment of an antibody), the antibody may specifically bind antigen positive cancer cells while the growth factor binds receptors on the surface of immune cells. The fusion protein may thus act to enhance and direct an immune response toward target cancer cells.

In Vitro Detection and Diagnostics

The method of using the compounds that bind to CD123 and their mimetics are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies and their mimetics are competitive and non-competitive immunoassays in either a direct or indirect format. Examples of such immunoassays are the radioimmunoassay (RIA) and the sandwich (immunometric) assay. Detection of antigens using the monoclonal antibodies and their mimetics can be done utilizing immunoassays which are run in either the forward, reverse, or simultaneous modes, including immunohistochemical assays on physiological samples. Those of skill in the art will know, or can readily discern, other immunoassay formats without undue experimentation.

The compounds that bind CD123 and mimetics can be bound to many different carriers and used to detect the presence of CD123 bearing leukemia cells, including progenitor cells. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding various compounds, or will be able to ascertain such, using routine experimentation.

For purposes of the invention, CD123 may be detected by the compounds and their mimetics when present in biological fluids and tissues. Any sample containing a detectable amount of CD123 ectopeptide can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of CD123

In using the CD123 binding compounds and mimetics for the in vivo detection of CD123, the detectably labeled compound or its mimetic is given in a dose which is diagnostically effective. The term "diagnostically effective" means that the amount of detectably labeled compound, such as monoclonal antibody or mimetic is administered in sufficient quantity to enable detection of the leukemia cells for which the compounds or mimetics are specific.

The concentration of detectably labeled compound or mimetic which is administered should be sufficient such that the binding to CD123 or CD123-bearing leukemia cells, is detectable compared to the background. Further, it is desirable that the detectably labeled compound or mimetic be rapidly cleared from the circulatory system in order to give the best target-to-background signal ratio.

As a rule, the dosage of detectably labeled compound or mimetic for in vivo diagnosis will vary depending on such factors as age, sex, and extent of disease of the individual. The dosage of the compound can vary from about 0.01 mg/kg to about 500 mg/kg, preferably about 0.1 mg/kg to about 200 mg/kg, most preferably about 0.1 mg/kg to about 10 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to the compound either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies and mimetics of the invention are $^{111}$In, $^{97}$Ru, $^{67}$Ga, $^{68}$Ga, $^{72}$As, $^{89}$Zr, $^{99m}$Tc, $^{123}$I and $^{201}$Tl.

In the diagnosis method of the invention, the compounds and mimetics can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

In the cell monitoring method of the invention, the compounds and mimetics can be used in vitro and in vivo to monitor the course of leukemia disease therapy. Thus, for example, by measuring the increase or decrease in the biological molecules associated with such a diseases or changes in the concentration of CD123 ectopeptide or CD123 bearing leukemia cells present in the body or in various body fluids, it would be possible to determine whether a particular therapeutic regimen aimed at ameliorating the above leukemia disease is effective.

Prophylaxis and Therapy of Leukemia

The CD123 specific compounds can also be used therapeutically for treatment of leukemia in both humans and other animals. The term, "therapeutically" or "therapy" as used herein in conjunction with the method of the invention is directed to using CD123 binding compounds, such as anti-CD123 monoclonal antibodies and their mimetics, which denotes both prophylactic as well as therapeutic administration and both passive immunization with substantially purified polypeptide products, and mimetics, as well as gene therapy by transfer of polynucleotide sequences encoding the product or part thereof. Thus, the compounds and mimetics can be administered to high-risk subjects in order to lessen the likelihood and/or severity of leukemia relapse, or administered to subjects already evidencing active leukemia disease.

For certain applications, it is envisioned that pharmacologic agents will serve as useful agents for attachment to the compounds, particularly cytotoxic or otherwise anticellular agents having the ability to kill or suppress the growth or cell division of leukemia cells. In general, the invention contemplates the use of any pharmacologic agent that can be conjugated to a CD123 binding compound and delivered in active form to the targeted cell. Exemplary anticellular agents include chemotherapeutic agents, radioisotopes as well as cytotoxins. In the case of chemotherapeutic agents, the inventors propose that agents such as a hormone such as a steroid; an antimetabolite such as cytosine arabinoside, fluorouracil, methotrexate or aminopterin; an anthracycline; mitomycin C; a vinca alkaloid; demecolcine; etoposide; mithramycin; calicheamicin, CC-1065 and derivatives thereof, or an alkylating agent such as chlorambucil or melphalan, will be particularly preferred. Other embodiments may include agents such as a coagulant, a cytokine, growth factor, bacterial endotoxin or the lipid A moiety of bacterial endotoxin. In any event, it is proposed that agents such as these may be successfully conjugated to antibodies in a manner that will allow their targeting, internalization, release or presentation to blood components at the site of the targeted leukemia cells as required using known conjugation technology.

In certain preferred embodiments, cytotoxic agents for therapeutic application will include generally a plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. The use of toxin-antibody constructs is well known in the art of immunotoxins, as is their attachment to antibodies. Of these, a particularly preferred toxin for attachment to antibodies will be a deglycosylated ricin A chain. Deglycosylated ricin A chain is preferred because of its extreme potency, longer half-life, and because it is economically feasible to manufacture a clinical grade and scale.

In other preferred embodiments, the cytotoxic agent may be a radioisotope. Preferred radioisotopes include α-emitters such as, for example, $^{211}$Astatine, $^{212}$Bismuth and $^{213}$Bismuth, as well as β-emitters such as, for example, $^{131}$Iodine, $^{90}$Yttrium, $^{177}$Lutetium, $^{153}$Samarium and $^{109}$Palladium.

As used herein, a "therapeutically effective amount" of a compound is a dosage large enough to produce the desired effect in which the symptoms of leukemia or the likelihood of onset of leukemia is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage may be adjusted by the individual physician or veterinarian in the event of any complication. A therapeutically effective amount may vary from about 0.01 mg/kg to about 500 mg/kg, preferably from about 0.1 mg/kg to about 200 mg/kg, most preferably from about 0.2 mg/kg to about 20 mg/kg, in one or more dose administrations daily, for one or several days.

In the method of the invention, the compounds and their mimetics can be administered by injection or by gradual infusion over time. The administration of the compounds and their mimetics may be, for example, intravenous, intraperitoneal, intramuscular, intracavity, subcutaneous, or transdermal.

Preparations for parenteral administration include sterile aqueous or non-aqueous solutions. suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions will include a conventional carrier or vehicle and a CD123 binding compound and, in addition, may include other medicinal agents, pharmaceutical agents, carriers, adjuvants, and so on.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, and so on.

The compounds of this invention are generally administered as a pharmaceutical composition which comprises a pharmaceutical vehicle in combination with a CD123 binding compound. The amount of the drug in a formulation can vary within the full range employed by those skilled in the art, e.g., from about 0.01 weight percent (wt %) to about 99.99 wt % of the drug based on the total formulation and about 0.01 wt % to 99.99 wt % excipient.

The preferred mode of administration, for the conditions mentioned above, is oral administration using a convenient daily dosage regimen which can be adjusted according to the degree of the complaint. For said oral administration, a pharmaceutically acceptable, non-toxic composition is formed by the incorporation of the selected CD123 binding compound in any of the currently used excipients, such as, for example, pharmaceutical grades of mannitol, lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between about 0.01 wt % and 99.99 wt % of the active compound according to this invention.

Preferably the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyrrolidone, acacia gum, gelatin, cellulose and derivatives thereof, and the like.

It is understood that by "pharmaceutical composition", it is meant that the CD123 binding compound is formulated into a substance that is to be administered purposefully diagnosing or treating leukemia in the individual. And, by "pharmaceutical composition", it excludes those compositions that are used to administer to individuals as test compounds for a purpose other than as a diagnostic or treatment agent for leukemia.

The invention is described in further detail hereinbelow.

Several recent studies have suggested the presence and importance of stem cells in both the genesis and perpetuation of AML. Phenotypically, cells described as CD34+/CD38− or CD34+/HLA-DR− appear to play a central role in the development of leukemic populations (Bonnet D, et al., Human acute myeloid leukemia is organized as a hierarchy that originates from a primitive hematopoietic cell. Nat. Med. 1997, 3: 730-737; Blair A, et al., Most acute myeloid leukemia progenitor cells with long-term proliferative ability in vitro and in vivo have the phenotype CD34(+)/CD71(−)/HLA-DR−. Blood 1998, 92: 4325-35). Furthermore, there is evidence suggesting that such cells may be relatively resistant to chemotherapeutic drugs, and consequently contribute to the phenomenon of relapse (Terpstra W, et al., Fluorouracil selectively spares acute myeloid leukemia cells with long-term growth abilities in immunodeficient mice and in culture. Blood 1996, 88: 1944-50). Thus, a better understanding of LSC biology and the characterization of unique LSC antigens are essential to the development of better treatments for AML.

While the various AML subtypes display considerable diversity with respect to developmental characteristics, phenotype, cytokine responsiveness, etc., there appears to be a marked degree of functional conservation at the level of more primitive leukemic cells. This feature has been demonstrated by the work of Bonnet et. al., in which a CD34+/CD38− subpopulation was shown to be sufficient to establish leukemia in NOD/SCID mice (Bonnet D, et al., Human acute myeloid leukemia is organized as a hierarchy that originates from a primitive hematopoietic cell. Nat. Med. 1997, 3: 730-737). Similar studies by others have corroborated the existence of leukemic stem cells for both AML and CML and confirmed their relatively homogeneous phenotype and functional capacity (Blair A, Hogge et al., Most acute myeloid leukemia progenitor cells with long-term proliferative ability in vitro and in vivo have the phenotype CD34(+)/CD71(−)/HLA-DR−. Blood 1998, 92: 4325-35; Holyoake T, et al., Isolation of a highly quiescent subpopulation of primitive leukemic cells in chronic myeloid leukemia. Blood 1999, 94: 2056-64). However, to date, no study has identified an antigenic feature of myeloid LSC's that may allow their identification or preferential targeting for ablative therapy. In this report, we have identified an additional commonality among CD34+/CD38− AML stem cells, expression of CD123, which facilitates their discrimination from normal hematopoietic stem cells. While the CD123 antigen was readily detected at high levels on AML cells, the IL-3 receptor β chain, CD131, was not detected.

Our experiments indicate that the transcription factor IRF-1 (Interferon regulatory factor-1) is over-expressed (in 6 of 6 primary AML specimens examined). Previous studies by Korpelainen et. al. have shown that treatment of endothelial cells with IFN-γ results in up-regulation of CD123 (Korpelainen E I, et al., Interferon-gamma upregulates interleukin-3 (IL-3) receptor expression in human endothelial cells and synergizes with IL-3 in stimulating major histocompatibility complex class II expression and cytokine production. Blood 1995, 86: 176-82). Similarly, our own studies have shown that treatment of primary AML cells with IFN-γ increases expression of CD123 (data not shown). Thus, aberrant expression of interferon regulatory molecules might play a role in controlling CD123 expression in AML cells.

Expression of the CD123 antigen formally demonstrates that LSC's are biologically distinct from their normal stem cell counterparts. Because CD123 is not readily found on normal hematopoietic stem cells, it provides a unique marker that can be used to identify malignant tissue. This feature may be useful for research purposes, as well as in minimal residual disease (MRD) studies. Further, the CD123 epitope represents a target to which therapeutic strategies may be directed. Previous clinical trials have used monoclonal antibodies against both the CD33 and CD45 antigens as a means to deliver radioisotopes to AML cells in vivo (Appelbaum F R., Antibody-targeted therapy for myeloid leukemia. Semin Hematol 1999, 36: 2-8.). In addition, several other recent studies have shown exciting results using monoclonal antibodies specific to antigens on malignant cells such as CD20, CD52, and Her-2 (Maloney D G., Advances in immunotherapy of hematologic malignancies. Curr Opin Hematol 1998; 5: 237-43; Sikic B I., New approaches in cancer treatment. Ann Oncol 1999, 10 Suppl 6: 149-53). Antibodies to CD123 may be useful in a similar paradigm and will be capable of delivering a cytotoxic hit that specifically targets the leukemic stem cell population.

We have shown that CD123 represents a unique antigenic marker for the identification of primitive leukemic cells from a broad range of human specimens across a broad range of leukemic diseases. Our studies show that CD123 is generally expressed at high levels and may be indicative of previously uncharacterized aspects of leukemia biology.

The present invention will be further illustrated in the following, non-limiting Examples. The Examples are illustrative only and do not limit the claimed invention regarding the materials, conditions, process parameters and the like recited herein.

EXAMPLES

Example 1

Materials and Methods: Cell Processing

Primary AML cells were obtained from the peripheral blood or bone marrow of patients. Normal bone marrow was obtained as waste material following pathological analysis, surgical marrow harvest, or from the National Disease Research Interchange (NDRI). Marrow cells were depleted of erythrocytes by suspending in 150 mM $NH_4Cl$+10 mM $NaHCO_3$ for 5 minutes, followed by two washes with phosphate buffered saline (PBS). Blood cells were subjected to Ficoll-Paque (Pharmacia) density gradient separation to isolate the mononuclear white blood cell compartment. Resulting leukocytes from marrow or blood were then used for immunoaffinity selection, and/or flow cytometric analysis or sorting. For CD34+ cell selection, the Miltenyi immunoaffinity device (varioMACS) was used according to the manufacturer's instructions. In some cases, leukocytes were cryopreserved at a concentration of $5\times10^7$ cells/ml in freezing medium consisting of Iscoves modified Dulbecco medium (IMDM), 40% fetal bovine serum (FBS) and 10% dimethylsulfoxide (DMSO).

Example 2

Flow Cytometry

Cytokine receptors were detected by labeling with the following monoclonal antibodies: CD114-biotin, CD116-FITC, CD123-PE, CD131-biotin (all from Pharmingen), CD117-PE (Coulter), and CD135-PE (Caltag). Biotinylated antibodies were visualized by subsequent labeling with streptavidin-PE (SA-PE, Becton Dickinson). Primitive AML subpopulations were identified using CD34-FITC or CD34-PE in combination with CD38-APC (Becton Dickinson). Primary AML cells were identified in NOD/SCID mice using CD45-PE (Pharmingen) specific to human cells. To analyze cells transplanted into NOD/SCID mice, bone marrow was harvested at 6-8 weeks post-transplantation. Cells were blocked with the anti-Fc receptor antibody 2.4G2 and 25% human serum, followed by double-labeling with human-specific CD34-FITC and CD45-PE antibodies. Control samples consisted of marrow cells from non-transplanted mice. In some cases, cells were also labeled with CD123-PE to ensure sustained expression of the CD123 antigen. For each specimen 50,000-100,000 events were analyzed. Using this approach, human cells could reliably be detected to a frequency as low as 0.1%. Any analysis falling below 0.1% positive cells was considered negative.

Example 3

Immunoblots

Cell samples were lysed at a concentration of $2\times10^7$ cells/ml in PBS containing: 1% NP-40, 0.5% deoxycholate, 0.1% sodium dodecyl sulfate (SDS), 1 mM sodium vanadate ($Na_3VO_4$), 30 µl aprotinin (Sigma), 1 mM phenylmethylsulfonyl fluoride (Sigma), 1 µg/ml pepstatin, and 1 µg/ml leupeptin (Oncogene Research); incubated on ice for 30 minutes, and centrifuged at 15,000×g for 10 minutes to remove debris. The resulting protein lysate was then aliquoted and stored at −80° C. For immunoblot analysis, protein lysates were thawed and mixed with sample buffer and reducing agent (Novex, San Diego, Calif., per manufacturer's instructions), and heated at 70° C. for 10 minutes. Samples were then immediately analyzed by denaturing PAGE (Novex, 4-12% Bis-Tris or 7% Tris-Acetate gels) using the equivalent of $4\times10^5$ cells per lane. Following electrophoresis, samples were electro-transferred onto Immobilon-P membrane (Millipore) and probed with the indicated antibodies. To detect CD123 (IL-3R alpha chain), antibodies S-12 (Santa Cruz Biotech) or 9F5 (Pharmingen) were used. For the analysis of Mek and Akt, protein-specific and phosphoprotein-specific rabbit polyclonal antibodies from New England Biolabs were used. Anti-Stat5 polyclonal (Transduction Labs) and anti-phospho-Stat5 (New England Biolabs) were used to analyze the phosphorylation status of Stat5. All primary antibodies were detected using alkaline phosphatase-conjugated secondary antibodies (Santa Cruz Biotechnology) and the ECF reagent (Pharmacia Biotech) per manufacturer's instructions. Blots were visualized using a Molecular Dynamics STORM 860 system and Imagequant™ Software.

Example 4

NOD/SCID Mouse Assays

NOD/SCID mice (Jackson Laboratories, Bar Harbor, Me.) were exposed to 225 rads of γ-irradiation from a $^{137}Cs$ source. Cells to be assayed were resuspended in 0.25 mls HBSS (Hanks balanced salt solution, Gibco) with 2% FBS and injected IV into the tail vein. For the analysis of some sorted populations, $1\times10^6$ irradiated (2500 Rads) mouse bone marrow cells were co-injected as carrier. After 6-8 weeks, animals were sacrificed and bone marrow was analyzed for the presence of human cells using flow cytometry (see above).

Example 5

Results

Figure 1B:
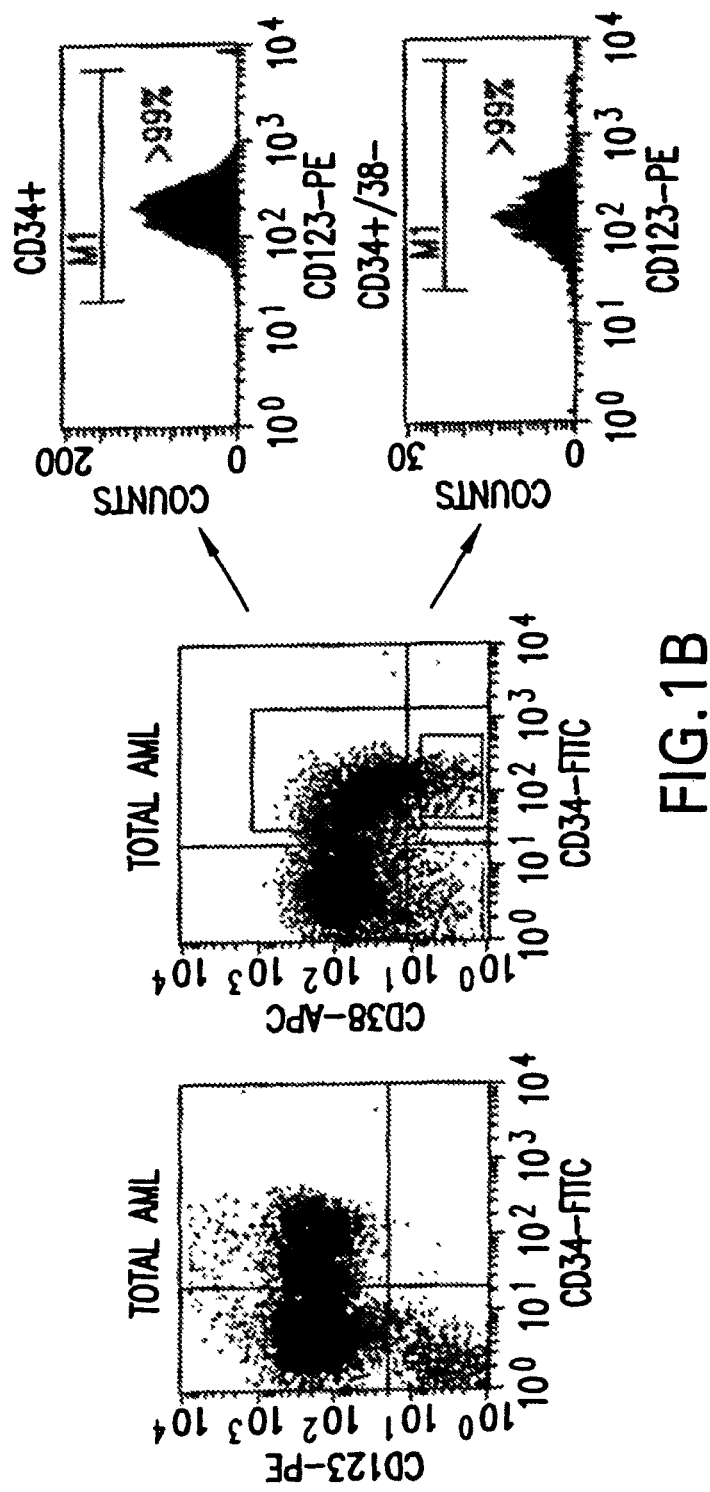
Figure 2A:
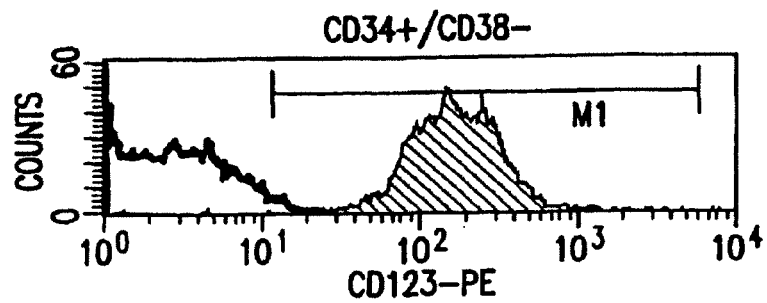
FIG. 2 shows CD expression on five primitive AML populations. Five primary AML specimens were labeled with CD34, CD38, and CD123 and analyzed by flow cytometry. The figure shows CD123 labeling for the CD34+/CD38− gated populations from each sample. The dark sections indicate CD123 staining and the light sections indicate parallel labeling with an isotype control antibody. M1 markers in the histograms indicate expression levels that are higher than 99% of isotype control samples. For each specimen, 50,000-100,000 events were analyzed.
Figure 2B:
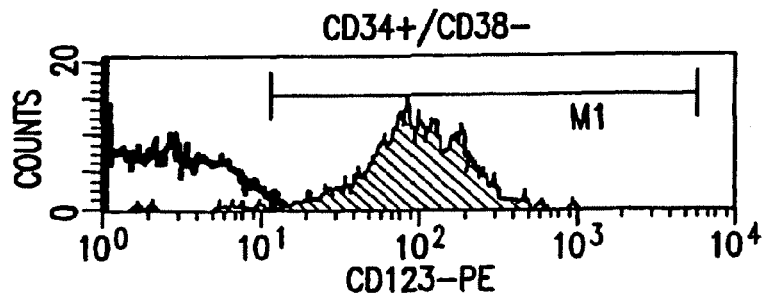
Figure 2C:
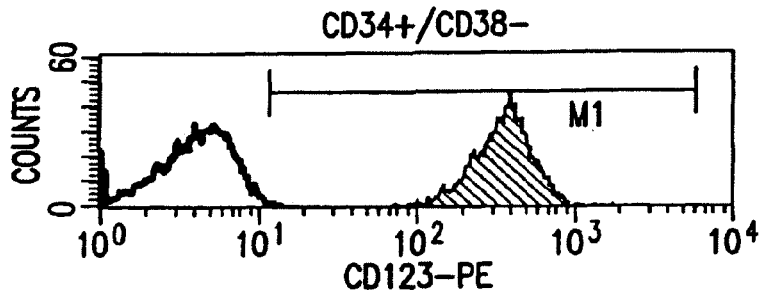
Figure 2D:
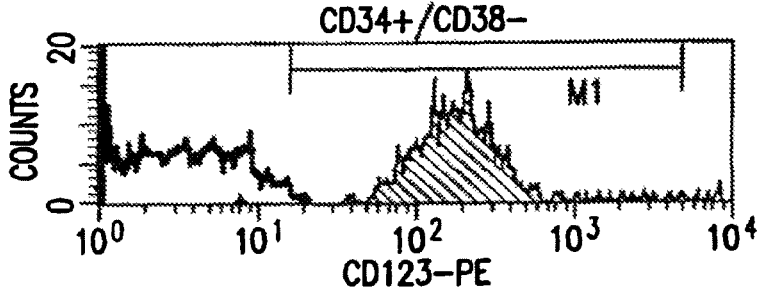
Figure 2E:
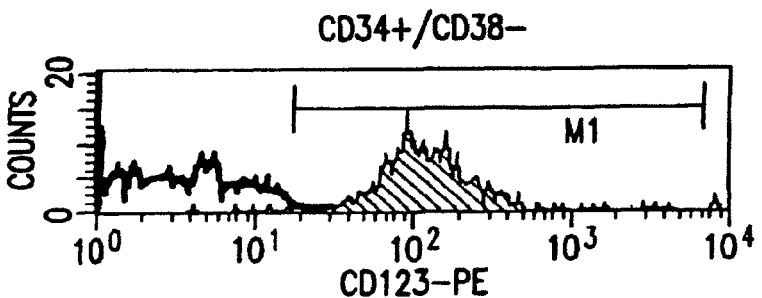

Analysis of cytokine receptors demonstrates strong expression of CD123 on primitive leukemic but not normal cells. Multiparameter flow cytometry was used to analyze the expression of cytokine receptors previously implicated in the growth of malignant hematopoietic cells. While several receptors displayed interesting patterns of antibody labeling, the most striking feature observed was a remarkably high and well-conserved level of CD123 (IL-3R alpha chain) expression amongst primary AML specimens. FIG. 1 shows representative examples of CD123 labeling in normal and leukemic tissue. In FIG. 1A total normal marrow, as well as more primitive subsets, are shown with respect to CD123 expression. Total marrow generally has about 7% positive cells for CD123, but only about 1% of the population expresses the antigen at high levels (see inset FIG. 1A). The CD34+ population of normal marrow also has readily evident CD123 expression (12% in FIG. 1A, right histogram), as would be expected for a population known to contain hematopoietic progenitors. The labeling profile shown is in good agreement with previous studies by Sato et. al. that have also examined IL-3Rα levels on human CD34+ cells (Sato N, et al., Expression and factor-dependent modulation of the interleukin-3 receptor subunits on human hematopoietic cells. Blood 1993, 82: 752-61.). However, the more primitive CD34+/CD38− compartment shows no significant expression of CD123 (<1%). In contrast, primary AML cells (FIG. 1B) displayed high levels of CD123. In both the overall CD34+ population, as well as the more primitive CD34+/CD38− compartment, greater than 99% of the cells were positive for CD123. FIG. 2 shows five additional examples of CD123 labeling on CD34+/CD38− AML cells, further demonstrating the strong expression of this antigen on leukemic populations. Table 1 summarizes the experiments performed to date on the AML cell type, and shows CD123 levels for primitive cells of AML subtypes M1, M2, and M4. Of the 18 primary AML specimens examined, CD123 was strongly expressed on the primitive leukemia cells in all but two instances. The two samples which had lower CD123 levels (samples AML-11 and AML-14, Table I) both displayed a uniform shift in CD123 expression, but had an overall labeling intensity that was dimmer than most samples assayed. In many cases (9 of 18), CD123 negative cells were virtually undetectable (0% or less than 1%). Conversely, expression of CD123 was not detected on 3 of 5 normal samples of CD34+/CD38− cells and was barely detectable in two additional specimens (<1%). These flow cytometric analyses were confirmed using two different anti-CD123 monoclonal antibodies to insure that the results were not an artifact caused by the use of a particular antibody.

The high level of CD123 expression found on all AML subtypes examined implies that IL-3Rα might play a central role in creating or maintaining the leukemic state. To form the high affinity receptor for IL-3, both the α and β chains (CD123 and CD131 respectively) are necessary. Thus, expression of CD131 was also examined by flow cytometry on the AML specimens. Interestingly, while some expression was seen in bulk AML populations, in 15 of 15 specimens CD131 was never detected in the CD34+ compartment (data not shown).

Further data demonstrating CD123 expression in primary ALL and primary CML cells, as well as non-Hodgkin's lymphoma, are discussed in Examples 8 and 10.

Example 6

In Vivo Engraftment Properties of Human CD123+ Leukemia Cells in NOD/SCID Mice

Figure 3A:
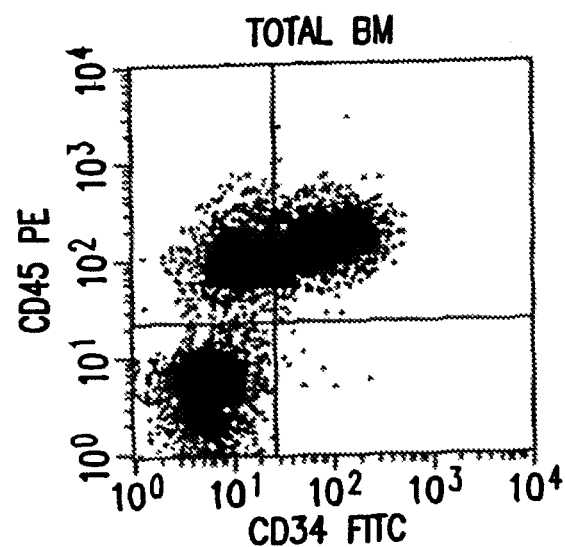
FIGS. 3A and 3B show engraftment of CD123+ AML cells in NOD/SCID mice. Sorted CD34+/CD123+ primary AML cells were transplanted into an irradiated NOD/SCID mouse. Six weeks post-transplant, bone marrow cells were isolated and analyzed for the presence of human (CD45+) leukemic cells. Panel A shows the CD34 vs. CD45 profile of an engrafted specimen using antibodies that are specific to human cells. Panel B shows the CD34 vs. CD123 profile of the CD45+ gated human cell population. For each sample, 50,000 events were analyzed.
Figure 3B:
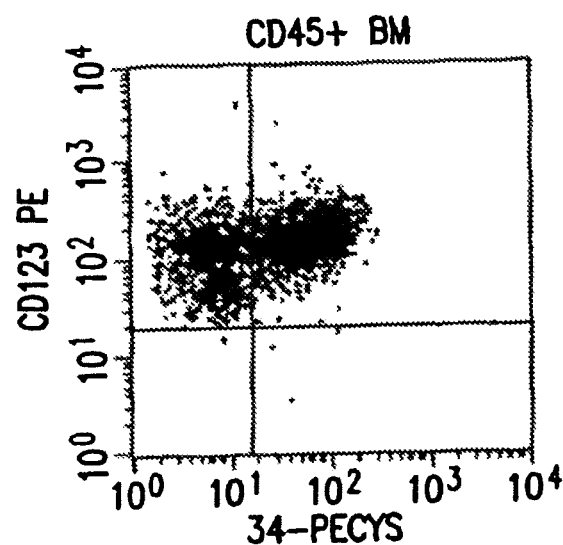

Given the strong CD123 expression observed on the vast majority of cells that phenotypically encompass the LSC population, it appeared likely that CD123 would be useful as a marker of LSC's. Therefore, to establish the functional capacity of CD123+ cells, transplantation studies using the NOD/SCID mouse model system were performed. Three primary AML specimens (AML-2, 5, and 15 from Table 1) were assayed by flow cytometrically sorting CD34+/CD123+ cells and transplanting them into irradiated NOD/SCID mice. In addition, the remaining cells in the population (CD34−/CD123+/−) were also sorted and transplanted in parallel. The data in FIG. 3 are a representative example of one specimen that showed strong engraftment of leukemic cells at six weeks post-engraftment. Panel A shows total bone marrow cells labeled with antibodies specific to human CD34 and CD45. The flow cytometric profile clearly indicates that a large population of human cells (CD45+) is present in the marrow. In addition, the population is divided between CD34+ and CD34− subsets, similar to the proportions of CD34 labeling seen in the original leukemic specimen. Panel B shows the same marrow sample gated only on the CD45+ cells. The data indicate that all of the cells that have proliferated in vivo are CD123 positive. Table 2 summarizes the data for the three specimens tested. In all cases, the CD123+ cells were capable of engrafting the NOD/SCID animals. Moreover, in all but one instance, the CD123− populations did not contribute to in vivo repopulation. Thus, as defined by the NOD/SCID model, we conclude that CD123 is expressed on the LSC.

Finally, as an independent means of confirming the leukemic origin of CD123 positive cells, flow cytometry was used to sort CD34+/CD123+ cells from two leukemic specimens. These samples were cultured for four days, synchronized and then harvested for cytogenetic analysis. Examination of spreads from each specimen showed that 20 out of 20 metaphases was positive for the leukemia-specific translocation.

Example 7

Biological Role of CD123 Expression in Leukemia Cells

Figure 4:
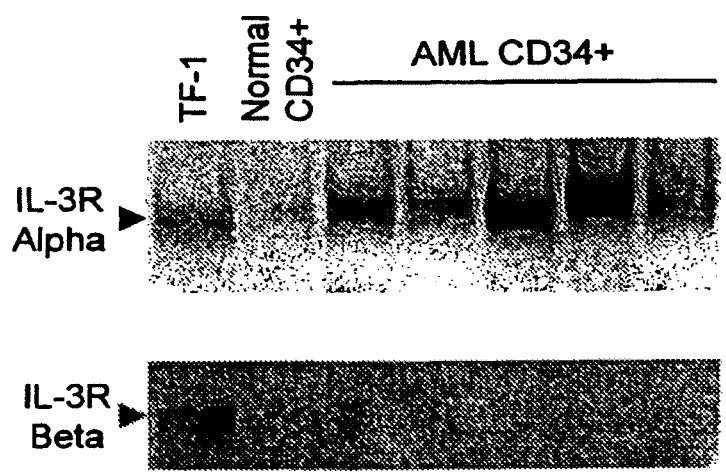
FIG. 4 shows CD123 and CD131 immunoblot analysis of primary AML specimens. Five primary AML samples were derived from peripheral blood and sorted to isolate the CD34+ population, thus insuring a virtually pure leukemic sample. In addition, the leukemic cell line TF-1 (TF-1) and normal marrow CD34+ cells (normal CD34+) were included as controls. Lysates were made from each population, subject to denaturing PAGE and analyzed by immunoblot with an anti-CD123 antibody (top panel) or an anti-CD131 antibody (bottom panel). The arrowhead at the left of each panel indicates the position of the IL-3Rα (CD123) and IL-3Rβ (CD131) chains, respectively.

To further corroborate the data obtained by flow cytometry, immunoblot studies were performed to analyze IL-3R signal transduction components. For these studies, each AML sample was derived from a peripheral blood specimen and was sorted to isolate the CD34+ population, thus insuring a virtually pure leukemic sample. First, expression of both the IL-3Rα and β chains were examined. With respect to CD123, the data shown in FIG. 4 (top panel) clearly demonstrate expression in all leukemic samples assayed. The CD34+ cells derived from normal marrow (lane 2, CD34+) also show a weak signal. This is consistent with the data in FIG. 1A, which show that normal CD34+ cells often contain a small subset of CD123+ cells. However, CD123 expression was not detected by flow cytometry in the more primitive CD34+/CD38− subset of normal cells (FIG. 1A and Table 1). Due to their low frequency, it was not possible to obtain sufficient CD34+/CD38− cells of either normal or AML origin for direct analysis by immunoblot. Nonetheless, detection of a clear signal in the overall CD34+ population corroborates the strong signal seen by flow cytometry for AML cells. Another point to note is that the molecular weight of the CD123 band appears to vary slightly between AML samples. We have performed RT-PCR fingerprint analyses of the same specimens and seen no obvious aberrancies (data not shown). Thus, it appears that varying degrees of post-translational modification are the most likely explanation for this observation. Consistent with the results obtained by flow cytometry, expression of CD131 was not detected (FIG. 4, bottom panel).

Figure 5A:
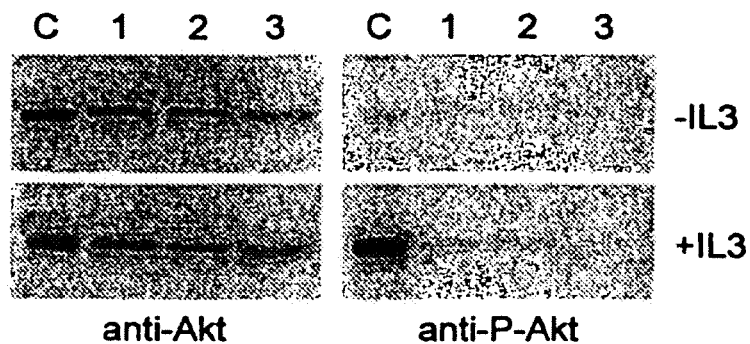
FIGS. 5A, 5B and 5C show phosphorylation of signal transduction components in response to IL-3. Three primary AML samples (Lanes 1-3) were derived from peripheral blood and sorted to isolate the CD34+ population. Samples were treated with (+) or without (−) 20 ng/ml IL-3 for 15 minutes, then lysed and subjected to PAGE. Each gel was then electro-blotted and membranes were probed with antibodies specific to either total or phosphorylated protein for Akt (A), Stat5 (B), and Mek-1(C). The lane labeled C on each blot is an antibody control and is derived from NIH 3T3 cells treated +/−50 ng/ml PDGF (A and C), or TF-1 cells treated +/−25 ng/ml GM-SCF (B).
Figure 5B:
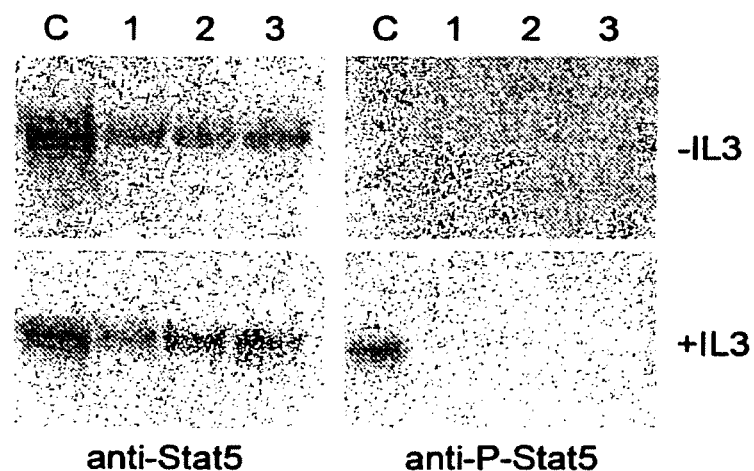
Figure 5C:
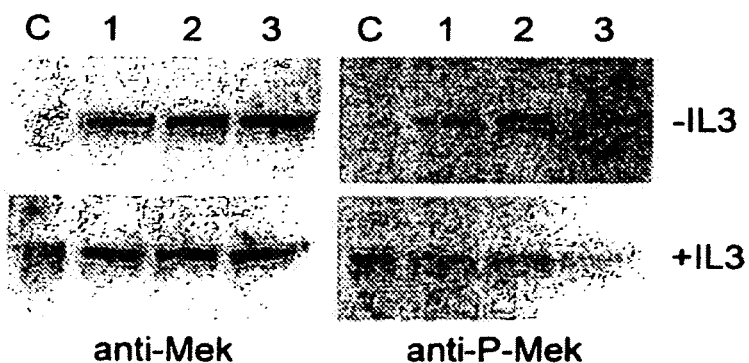

To begin exploring a potential functional role for CD123, we examined the response of primary AML cells to IL-3. Typically, stimulation of hematopoietic cells with IL-3 leads to several well-characterized intracellular signal transduction events (Hara T, et al., Function and signal transduction mediated by the interleukin 3 receptor system in hematopoiesis. Stem Cells 1996, 14: 605-18). Prevalent among these events are phosphorylation of Mek-1, Akt, and Stat-5 (Songyang Z, et al., Interleukin 3-dependent survival by the Akt protein kinase. Proc Natl Acad Sci USA 1997, 94: 11345-50; Yagisawa M, et al., Signal transduction pathways in normal human monocytes stimulated by cytokines and mediators: comparative study with normal human neutrophils or transformed cells and the putative roles in functionality and cell biology. Exp Hematol 1999, 27: 1063-76; Sutor S L, et al., A phosphatidylinositol 3-kinase-dependent pathway that differentially regulates c-Raf and A-Raf. J Biol Chem 1999, 274: 7002-10; de Groot R P, et al., Regulation of proliferation, differentiation and survival by the IL-3/IL-5/GM-CSF receptor family. Cell Signal 1998, 10: 619-28). Consequently, immunoblot studies were performed on these proteins to assess the degree of phosphorylation, both in the presence or the absence of IL-3 stimulation. The data, shown in FIG. 5, show no detectable phosphorylation of Akt and Stat5 in the absence of IL-3, and only a moderate level of phosphorylation for Mek-1. Furthermore, in response to IL-3 stimulation, no appreciable increase in phosphorylation is seen for any of the proteins assayed. These results suggest that CD123 present on the surface of primary AML cells does not contribute significantly to signal transduction via conventional IL-3 mediated pathways.

Example 8

CD123 Expression in Primary ALL and Primary CML Cells

Figure 6A:
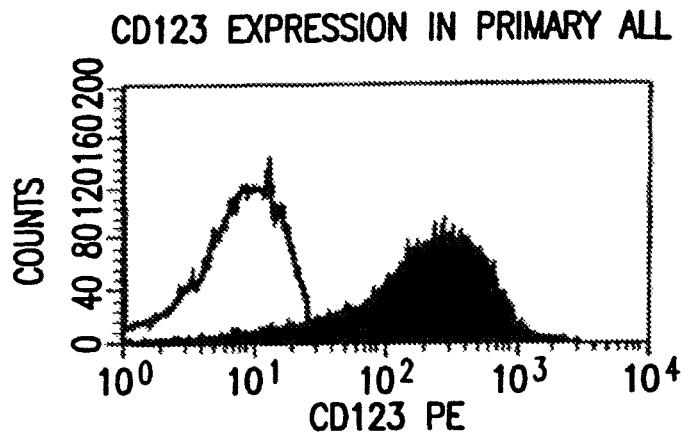
FIGS. 6A, 6B and 6C show CD123 expression in primary ALL. Flow cytometric analysis of CD123 expression on three independent primary ALL (acute lymphoid leukemia) specimens. CD123 labeling is shown by the filled (dark) plots and controls are shown by open plots.
Figure 6B:
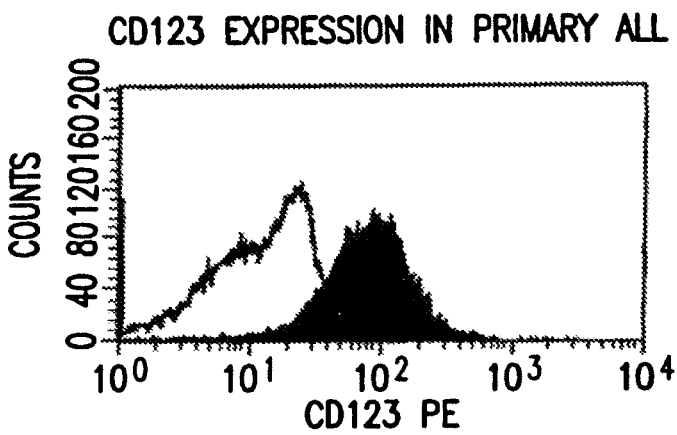
Figure 6C:
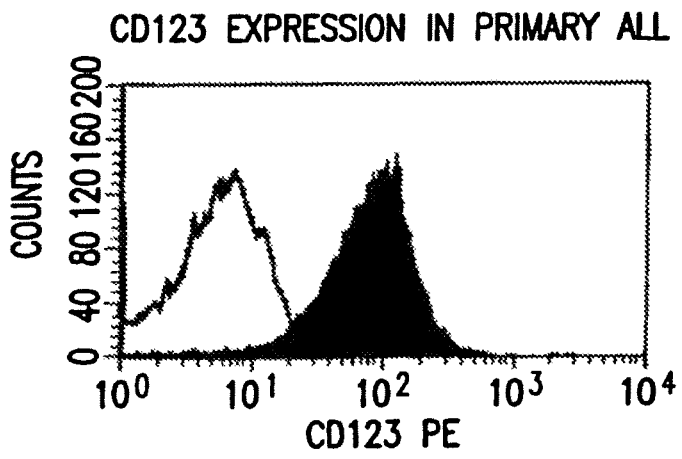
Figure 7A:
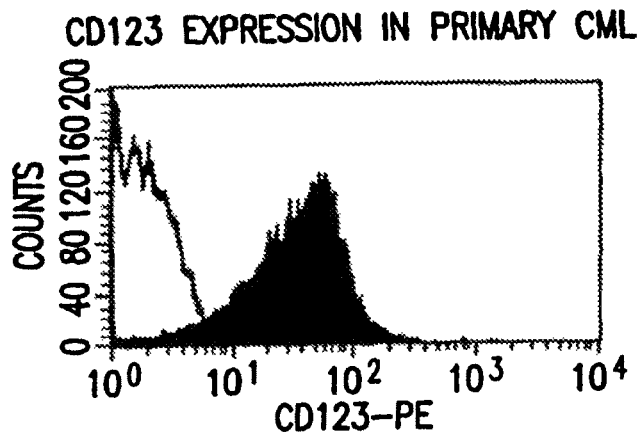
FIGS. 7A, 7B and 7C show CD123 expression in primary CML. Flow cytometric analysis of CD123 expression on three independent primary CML (chronic myelogenous leukemia) specimens. CD123 labeling is shown by the filled (dark) plots and controls are shown by open plots.
Figure 7B:
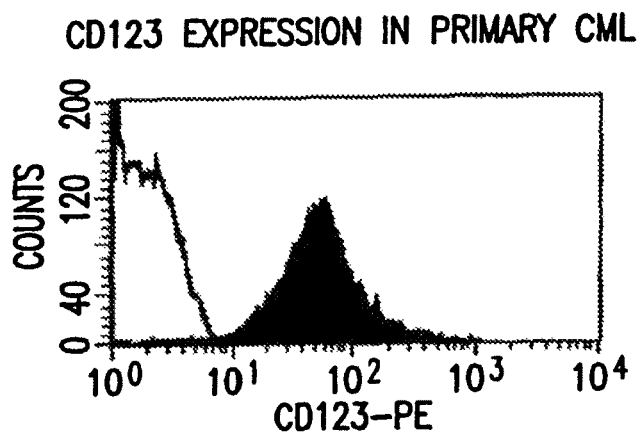
Figure 7C:
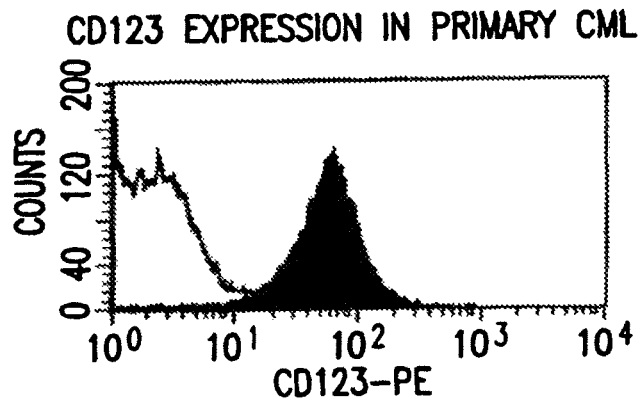

Similar experimental protocol as described in Examples 1 through 4 were followed, and the expression of CD123 was assayed in primary ALL and primary CML cells by flow cytometry. The results were consistent with the results obtained with expression of CD123 in primary AML in Example 5. FIGS. 6A, 6B, and 6C show reproducibly that the primary ALL cells express CD123. Moreover, FIGS. 7A, 7B, and 7C show reproducibly that the primary CML cells also express CD123.

Example 9

CD123 Targeted Complement-Kill Assay

By using a complement-kill assay, "Current protocols in Immunology" Edited by John Coligan, Ada Kruisbeek, David Margulies, Ethan Shevach, and Warren Strober, John Wiley and Sons publishing, 1992, which is incorporated by reference herein in its entirety, this experiment demonstrates that CD123+ cells are preferentially targeted. In this experiment, we compared a typical AML specimen (i.e. CD123+) to a normal bone marrow sample. For each specimen there is an untreated control, a sample treated with complement alone, and a sample treated with anti-CD123+ complement. As shown in Table 3, there is a substantial complement-killing effect on the AML specimen, but no effect on the normal marrow. This is true for both the overall sample, as well as the more primitive CD34+ cells. Accordingly, this experiment demonstrates that there is a difference between the effect on normal and leukemic cells with respect to the specificity for CD123.

Example 10

CD123 Expression in Lymphoma Cells

Immunohistochemical analysis of tissue sections showed that "diffuse large B cell lymphoma" is strongly positive for expression of CD123. This is the most common form of non-Hodgkin's lymphoma. Thus, in a B-cell derived cancer, expression of CD123 is consistent with the observation that CD123 was also observed on ALL cells (i.e. another type of B cell cancer). This observation directly identifies B cell lymphomas as a target for therapies and diagnostics using CD123.

All of the cited references are incorporated by reference herein in their entirety.

Those skilled in the art will recognize, or be able to ascertain using no more than routine experimentation, many equivalents to the specific embodiments of the invention specifically described herein. Such equivalents are intended to be encompassed in the scope of the following claims.

TABLE 1

Expression of CD123 in Primitive Leukemic and Normal Cells.

| Specimen | FAB | % CD123+ cells in CD34+/CD38− population |
|---|---|---|
| AML | | |
| AML-1 | MDS/AML | 100% |
| AML-2 | M1 | 100% |
| AML-3 | M1 | 95.2% |
| AML-4 | M4 | 98.1% |
| AML-5 | M2 | 99.7% |
| AML-6 | M4 | 99.5% |
| AML-7 | nd | 100% |
| AML-8 | M4 | 99.7% |
| AML-9 | M4 | 99.8% |
| AML-10 | M2 | 100% |
| AML-11 | MDS/AML | 70.2% |
| AML-12 | nd | 92.5% |
| AML-13 | M1 | 97.5% |
| AML-14 | M4 | 51.1% |
| AML-15 | M4 | 98.1% |
| AML-16 | M1 | 95.3% |
| AML-17 | M1 | 98.9% |
| AML-18 | M4 | 100% |
| Normal Marrow | | |
| BM-1 | na | 0 |
| BM-2 | na | <1% |
| BM-3 | na | 0 |
| BM-4 | na | 0 |
| BM-5 | na | <1% |

FAB = French, American, British classification system
MDS/AML = myelodysplastic syndrome progressing to AML
na = not applicable

TABLE 2

Engraftment of CD123+ Populations in NOD/SCID Mice.

| Exp. | Specimen | Population Assayed (N) | Cells Inj./mouse | % CD45+ cells/recip. |
|---|---|---|---|---|
| 1 | AML-2 | CD34+/CD123+ (3) | 4.9 × 10e6 | 42% |
| | | | | 18% |
| | | | | 67% |
| | | CD34−/CD123+/− (3) | 7.5 × 10e5 | nd |
| | | | | 0.2% |
| | | | | 0.1% |
| 2 | AML-5 | CD34+/CD123+ (4) | 2.5 × 10e6 | 15% |
| | | | | 6% |
| | | | | 1% |
| | | | | 12% |
| | | CD34−/CD123+/− (3) | 2.5 × 10e6 | nd |
| | | | | nd |
| | | | | nd |
| 3 | AML-15 | CD34+/CD123+ (5) | 2.1 × 10e6 | 2.1% |
| | | | | 0.2% |
| | | | | 0.8% |
| | | | | 1.1% |
| | | | | 0.9% |
| | | CD34−/CD123+/− (3) | 2.4 × 10e6 | nd |
| | | | | nd |
| | | | | nd |

N = number of mice assayed
nd = not detectable

TABLE 3

| CD123 Specific Complement-Kill Assay | | |
|---|---|---|
| | Viability | |
| | Total Cells | CD34+ |
| Primary AML specimen | | |
| unstained control | 68.53% | 73.29% |
| complement only | 67.76% | 77.17% |
| anti-CD123 + complement | 21.31% | 33.25% |
| Primary normal BM | | |
| unstained control | 80.20% | 78.20% |
| complement only | 79.42% | 80.33% |
| anti-CD123 + complement | 80.46% | 81.51% |

What is claimed is:

1. A method for reducing the number of CD123-bearing leukemia cells in a human diagnosed with acute myelogenous leukemia (AML),
said method comprising administering to the human a therapeutically effective amount of an antibody that binds CD123, such that said administration causes a reduction in the number of leukemia cells in the subject.

2. The method of claim 1, wherein the therapeutically effective amount is a dosage of about 0.01 mg/kg to about 500 mg/kg.

3. The method of claim 1, further comprising monitoring the amount of AML cells present in the human to determine the therapeutic effectiveness of the antibody.

4. The method of claim 1, further comprising monitoring the amount of CD123-bearing leukemia cells present in the human to determine the therapeutic effectiveness of the antibody.

5. The method of claim 1, wherein the therapeutically effective amount of the antibody is administered to the human daily or for one or several days.

6. The method of claim 1, wherein the antibody is a monoclonal antibody, $F(ab')_2$, Fab or Fv.

7. The method of claim 1, further comprising administering to the human an additional therapeutic agent.

8. The method of claim 7, wherein the additional therapeutic agent is a chemotherapeutic agent.

9. The method of claim 8, wherein the chemotherapeutic agent is a steroid, cytosine arabinoside, fluorouracil, methotrexate, aminopterin, an anthracycline, mitomycin C, a vinca alkaloid, demecolcine, etoposide, mithramycin, calicheamicin, CC-1065, chlorambucil, or melphalan.

10. The method of claim 1, wherein the antibody is administered intravenously, intramuscularly, subcutaneously, percutaneously, orally, parenterally, vaginally, ocularly, nasally, transdermally, or intraperitoneally.

* * * * *